US00PP13475P2

(12) United States Plant Patent
Bradford

(10) Patent No.: US PP13,475 P2
(45) Date of Patent: Jan. 14, 2003

(54) NECTARINE TREE NAMED 'SEPTEMBER BRIGHT'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/014,018

(22) Filed: Dec. 13, 2001

(51) Int. Cl.[7] ..... A01H 5/00
(52) U.S. Cl. ..... Plt./190; Plt./192
(58) Field of Search ..... Plt./190, 192

(56) References Cited

U.S. PATENT DOCUMENTS

PP5,664 P 2/1986 Bradford ..... Plt./190
PP6,363 P 11/1988 Bradford ..... Plt./190

*Primary Examiner*—Bruce R. Campell
*Assistant Examiner*—W C Haas

(57) ABSTRACT

The present invention relates to a nectarine tree, *Prunus persica* and more particularly to a new and distinct variety broadly characterized by a large side, vigorous, hardy, self-fertile, productive and regular bearing tree. The fruit matures under the ecological conditions described approximately the first week in September, with first picking on Sep. 1, 2001. The fruit is uniformly medium in size, very good in flavor, globose in shape, clingstone in type, firm in texture, yellow in flesh color, and red in skin color. The variety was developed as a first generation cross using 'August Red' (U.S. Plant Pat. No. 6,363) yellow flesh nectarine as the selected seed parent and an unnamed nectarine as the selected pollen parent.

1 Drawing Sheet

BOTANICAL CLASSIFICATION

*Prunus persica.*

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'SEPTEMBER BRIGHT'. The present variety was hybridized by me in 1992, grown as a seedling on its own root in my greenhouse, and transplanted to a cultivated area of my experimental orchard at Bradford Farms near Le Grand, Calif. in Merced County (San Joaquin Valley). The variety was developed as a first generation cross using 'August Red' (U.S. Plant Pat. No. 6,363) yellow flesh nectarine as the selected seed parent and an unnamed nectarine as the selected pollen parent. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is similar to its selected seed parent, 'August Red' (U.S. Plant Pat. No. 6,363) nectarine, by producing nectarines that are globose in shape, firm in texture, mostly red in skin color, and yellow in flesh color, but is distinguished therefrom and an improvement thereon by producing fruit that matures about two weeks later.

The present variety is most similar to 'September Red' (U.S. Plant Pat. No. 5,664) nectarine by producing nectarines that are yellow in flesh color and that mature in September, but is distinguished therefrom and an improvement thereon by having a small nonshowy blossom and by producing fruit that is firmer in texture, that has a higher percentage of red skin color, and that is larger in size.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin County), Calif., and was developed at the state of firm ripe on Sep. 10, 2001, on the original tree during its ninth growing season. All major color code designations are by reference to the Inter-Society Color Council, National Bureau of Standards. Common color names are also used occasionally.

Tree

Size: Large, reaching and maintaining a height of 13' [3.96 m.] after nine growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.
Production: Very productive, thinning necessary.
Fertility: Self-fertile.
Bearing: Regular bearer with no alternate bearing yet observed.
Trunk:
*Size.*—Medium, reaching a maximum diameter of 4½" [114 mm.] after the ninth growing season.
*Texture.*—Shaggy.
*Bark color.*—Brownish gray [64. brGy].
*Lenticels.*—Numerous. Color: Moderate orange yellow [71. m.OY]. Typical Size: ⅛" to 7/16" [3.2–11.1 mm.].
Branches:
*Size.*—Diameter of scaffold is 2½" [64 mm.] measured 12" above the crotch, typical of *Prunus persica*, and dependent upon cultural practices and climatic conditions.
*Texture.*—Smooth on 1st year wood, increasing roughness with age.
*Color.*—1st Year Wood Topside: Grayish red [19. gy.R]. 1st Year Wood Underside: Brilliant yellow green [116. brill.YG]. Older Wood: Moderate yellowish brown [77. m.yBr].
*Lenticels.*—Numerous. Color: Strong orange yellow [68. s.OY]. Size: Medium, 1/16" to 3/16" [1.6–4.8 mm.].
Leaves:
*Size.*—Medium. Average Length: 5⅝" [143 mm.]. Average width: 1⅝" [41 mm.].
*Arrangement.*—Alternate.
*Thickness.*—Medium.
*Form.*—Elliptical.
*Apex.*—Acuminate.
*Base.*—Acute to somewhat rounded.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Petiole.*—Average Length: 7/16" [11.1 mm.]. Average Thickness: 1/16" [1.6 mm.]. Color: Light yellow green [119. l.YG].
*Stipules.*—Number: 2 per leaf, up to 6 per growing tip. Average Length: 7/16" [11.1 mm.]. Color: Light yellow green [119. l.YG] when growing.
*Glands.*—Number: 2 to 4. Position: Alternately positioned on the petiole and base of blade. Size: Medium. Form: Reniform. Color: Brilliant yellow green [116. brill.YG] on newer leaves acquiring Dark reddish brown [44. d.rBr] centers on with age.
*Leaf buds.*—Pointed.
Flower buds:
*Hardiness.*—Hardy, with respect to central California winters.
*Diameter.*—Typically 5/16" [7.9 mm.] 1 week before bloom.
*Length.*—Typically 9/16" [14.3 mm.] 1 week before bloom.
*Form.*—Not appressed.
*Surface.*—Pubescent.
*Color.*—Strong purplish red [255. s.pR].
Flowers: Perfect, complete, perigynous, usually a single pistil, typically thirty or more stamens, five sepals and petal locations alternately positioned.
*Type.*—Nonshowy, small.
*Average flower diameter.*—⅞" [22.2 mm.].
*Number of petals.*—Usually five, with a few double blossoms.
*Petal shape.*—Oval.
*Petal margin.*—Wavy.
*Average petal diameter.*—5/16" [7.9 mm.].
*Average petal length.*—⅜" [9.5 mm.].
*Petal apex.*—Rounded.
*Petal base.*—Acute.
*Petal color.*—Moderate purplish red [258. m.pR].
*Anther color.*—Strong reddish orange [35. s.rO].
*Stigma color.*—Light yellow [86. l.Y].
*Sepal color.*—Grayish purplish red [262. gy.pR].
*Sepal length.*—5/32" [4 mm.].
*Sepal width.*—5/32" [4 mm.].
*Average pistil length.*—½" [12.7 mm.].
*Average stamen length.*—7/16" [11.1 mm.].
*Fragrance.*'Moderate when nectar is present.
*Blooming period.*—Medium compared with other varieties.
*Onset of bloom.*—One percent on Feb. 27, 2001.
*Date of full bloom.*—Mar. 7, 2001.
*Duration of bloom.*—One to two weeks, dependent on ambient temperature.
*Number per cluster.*—Mostly 1, occasionally 2, rarely more than 2.

FRUIT

Maturity when described: Firm ripe, Sep. 10, 2001.
Date of first picking: Sep. 1, 2001.
Date of last picking: Sep. 14, 2001.
Size: Uniform, medium.
*Average diameter axially.*—2 9/16" [65.1 mm.].
*Average diameter across suture plane.*—2¾" [69.9 mm].
*Typical weight.*—6.3 ounces [179 grams].
Form: Uniform, symmetrical, globose to slightly oblate.
*Longitudinal section form.*—Roundish, compressed toward the poles.
*Transverse section through diameter.*—Roundish.
Suture: A shallow groove toward the base increasing in depth and sharpness toward the apex, having a marked depression beyond the pistil point.
Ventral surface: Rounded, lipped toward the apex.
Lips: Equal toward the apex, but one side protruding more than the other along the mid suture area.
Cavity: Flaring, elongated in the suture plane, suture showing on one side, Brilliant yellow [83. brill.Y] stem markings typical.
*Depth.*—7/16" [11.1 mm.].
*Breadth.*—15/16" [23.8 mm.].
Base: Truncate.
Apex: Rounded, somewhat cuneate when viewed parallel to suture.
Pistil point: Apical, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—None observed.

*Color.*—Very deep red [14. v.deep R] mottled into a Strong red orange [35. s.rO] background with some Very yellow [82. v.Y] areas where sun protected.

Flesh:

*Color.*—Brilliant yellow [83. brill.Y] toward the skin with substantial Deep red [13. deep R] streaking toward the stone.

*Surface of pit cavity.*—Dark red [16. d.R] fibers breaking when twisted from the stone.

*Amygdalin.*—Abundant.

*Juice.*—Abundant, rich.

*Texture.*—Firm, crisp.

*Fibers.*—Abundant, fine.

*Ripens.*—Slightly earlier toward the apex.

*Flavor.*—Mildly acidic and sweet, averaging 13 brix.

*Aroma.*—Slight.

*Eating quality.*—Very good.

STONE

Type: Clingstone.
Form: Oval.
Hilum: Narrow.
Base: Straight.
Apex: Acute, with very little tip.
Sides: Slightly unequal.
Surface: Irregularly furrowed near the apex and pitted toward the base.
Ridges: Jagged toward the base.
Color: Moderate brown [58. m.Br].
Average pit wall thickness: ¼" [6.4 mm.].
Average width: 1" [25.4 mm.].
Average length: 1⅜" [34.9 mm.].
Tendency to split: Slight.
Kernel:

*Form.*—Oval.

*Pellicle color.*—Grayish brown [61. gy.Br].

*Skin color.*—Deep orange yellow [69. deep OY].

*Vein color.*—Moderate brown [58. m.Br].

*Taste.*—Very bitter.

*Viable.*—Yes.

*Average width.*—½" [12.7 mm.].

*Average length.*—¾" [19.1 mm.].

*Amygdalin.*—Abundant.

USE

Market: Fresh market and long distance shipping.
Keeping quality: Good. Fruit quality observed to remain in good condition in after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'September Red' (U.S. Plant Pat. No. 5,664) nectarine by producing nectarines that are yellow in flesh color and that mature in September, but is distinguished therefrom and an improvement thereon by having a small nonshowy blossom and by producing fruit that is firmer in texture, that has a higher percentage of red skin color, and that is larger in size.

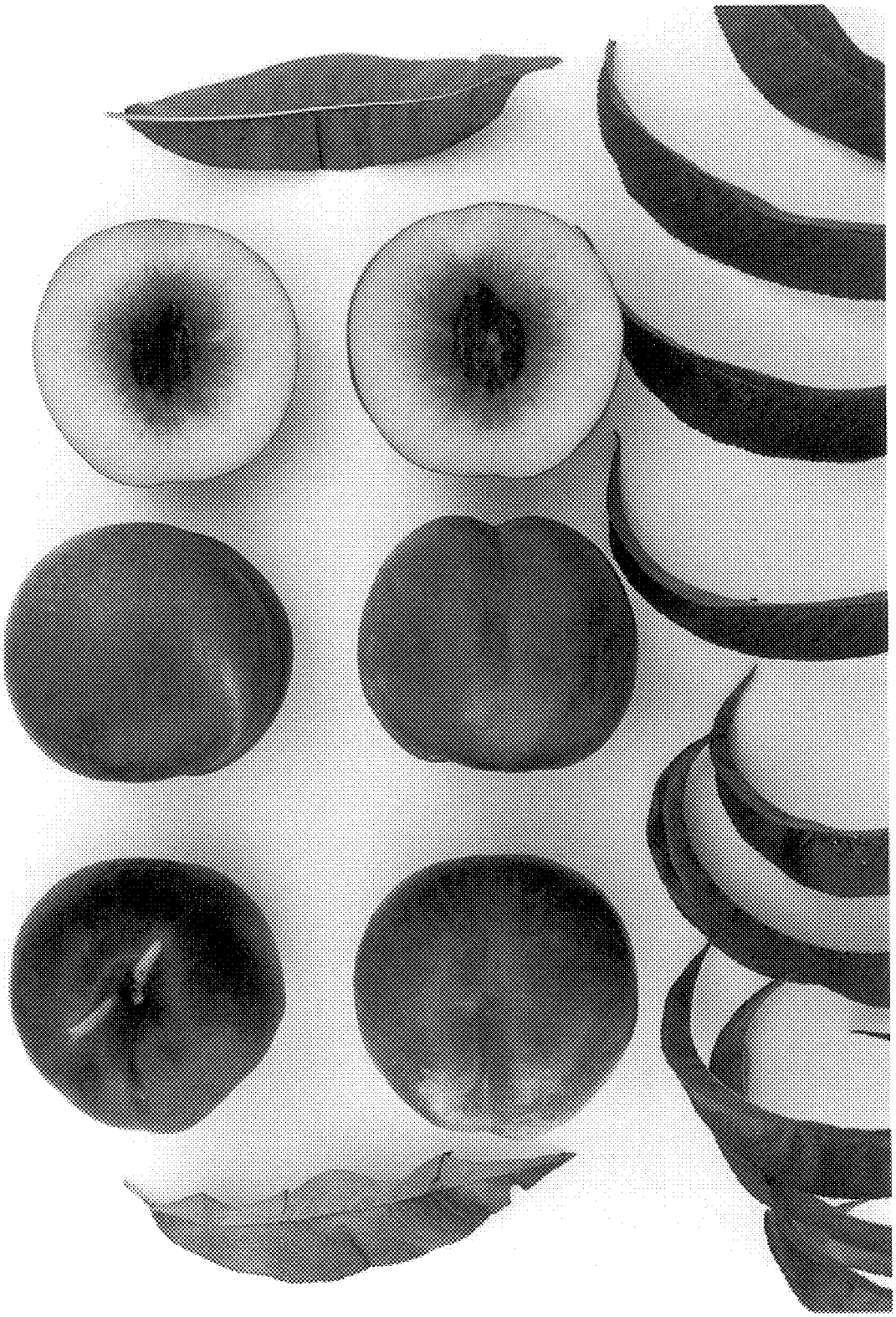

* * * * *